US006500192B1

(12) United States Patent
Werding

(10) Patent No.: US 6,500,192 B1
(45) Date of Patent: Dec. 31, 2002

(54) DEVICE FOR TREATING PERIPHERAL CIRCULATORY DISORDERS AND CLOSING DEVICE FOR A TREATMENT CYLINDER THEREOF

(76) Inventor: Winfried Werding, 20, rue du Carroz, 1278 La Rippe (CH)

( * ) Notice: Subject to any disclaimer, the term of this patent is extended or adjusted under 35 U.S.C. 154(b) by 0 days.

(21) Appl. No.: 09/554,411

(22) PCT Filed: Nov. 11, 1998

(86) PCT No.: PCT/IB98/01795

§ 371 (c)(1), (2), (4) Date: May 12, 2000

(87) PCT Pub. No.: WO99/25305

PCT Pub. Date: May 27, 1999

(51) Int. Cl.[7] ................................................ A61B 17/00
(52) U.S. Cl. ...................................................... 606/201
(58) Field of Search ................................ 606/201, 202, 606/203, 204; 128/202.12; 601/9, 11, 166, 152, 134, 107

(56) References Cited

U.S. PATENT DOCUMENTS 2,082,190 A 6/1937 Vogt et al.
2,113,253 A 4/1938 Gray
3,329,142 A 7/1967 MacLeod
4,624,248 A * 11/1986 Poole et al. ................ 606/201
6,007,559 A * 12/1999 Arkans ....................... 606/201

FOREIGN PATENT DOCUMENTS

AT 301746 9/1972
DE 8905848 U 8/1989
EP 0284772 A2 10/1988

* cited by examiner

*Primary Examiner*—Kevin T. Truong
(74) *Attorney, Agent, or Firm*—Young & Thompson

(57) ABSTRACT

The device comprises a treatment cylinder (1) into which one extremity (E) is placed for treatment of a peripheral circulatory disorder and subjected to hyperbaric and hypobaric phases. Said treatment cylinder has one end (B) that is hermetically closed, and on the other end (A) supports a sleeve (C) that consists of a thick-walled rubber disk (4) which on its flat sides is covered by thin-walled, highly elastic rubber membranes (6, 7). The rubber disk and the rubber membranes are provided with openings (5, 8, 9), while the diameters of the openings (8, 9) of the rubber membranes (6, 7) are smaller than the diameter of the opening (5) of the rubber disk (4) so that during pressure changes in the treatment cylinder (1) the rubber membranes (6, 7) adapt so to the form of the extremity (E) to be treated that they create a sleeve effect and close off the treatment cylinder (1) at the end (A) in such a way that the intensity of the pressure variation can be achieved and kept constant during a specific time period without having to inflate the sleeve (C). This solution prevents for the entire duration of the treatment the venous return to the heart from becoming blocked.

13 Claims, 7 Drawing Sheets

DEVICE FOR TREATING PERIPHERAL CIRCULATORY DISORDERS AND CLOSING DEVICE FOR A TREATMENT CYLINDER THEREOF

BACKGROUND OF THE INVENTION

The present invention concerns a device for the treatment of peripheral circulatory disorders that consists of at least one treatment cylinder into which a body limb to be treated can be introduced at least in part through a closing device, and in which by means of a device for the admission and evacuation of air and of control elements a compression or/and decompression can be created, and in particular the closing device for the treatment cylinder which prevents the veins from becoming obstructed when a compression or/and decompression is created in the treatment cylinder.

As early as 1834 JUNOD studied the effects of compression on the body or one of the body extremities and invented devices with which he took hyperbaric baths.

At the end of the $19^{th}$ century BIER subjected arms or legs to a decompression that caused a venous congestion which he put to use as a therapeutic measure for rheumatic pain.

1932 HERRMANN studied the literature concerning hypobaric treatments and found that this method could activate arterial blood flow in the extremities. In the same year he established that the effect was enhanced when an extremity was subjected to alternating hypobaric and hyperbaric phases.

Since that time the devices subsequently built possess programmes with hyperbaric and hypobaric phases. They had a cylinder consisting of glass or Plexiglas that was closed off with a rubber hose while advantage was taken of the elasticity of the rubber for closing.

This procedure inevitably brought about an obstruction of the veins and, depending on the intensity of the decompression, an obstruction of the arteries, so that the treatment as such only made use of the venous congestion that had been applied as a therapeutic measure by Bier.

One also knows inflatable boots made of flexible material (JOBST), but these can only exert a compression on an extremity, while the effect of this compression, since it is limited to the surface, never can attain the effect exerted by direct air pressure.

1956 the VASOTRAIN device appeared on the market, where the treatment cylinder was sealed with an inflatable sleeve. Despite this improvement of the method of exerting compression and decompression on an extremity, the VASOTRAIN also produced venous congestion, and BARBEY reports that because of the appearance of petechia, treatments with the VASOTRAIN had to be discontinued.

WERDING in 1960 designed the VASCULATOR, which also had inflatable sleeves, with the new feature, however, that these sleeves always maintained their pressure on the extremities at a minimum value, i.e., their internal pressure only rose until the desired compression was attained, whereupon a certain, intended loss of compression could be, both compensated with the pump or kept constant by slight inflation of the sleeve.

During automatic changeover of the device to decompression, the sleeve emptied continuously in proportion to the intensity of the decompression.

This method very largely reduced an obstruction of the veins, but not enough, as the VASCULATOR had to place the extremity in a high position in order to aid venous return to the heart.

It is the aim of the present invention to eliminate the problems of venous congestion described above, and it is proposed to provide a closing device for treatment cylinders which is capable of keeping even the veins that are located at the surface of an extremity, as pervious as possible during a hypobaric phase.

SUMMARY OF THE INVENTION

According to the invention, this problem is resolved by the fact that the closing device is provided with a sleeve having a thick-walled disk covered on its two flat sides by thin-walled, highly elastic membranes, that the disk is provided with a first opening and the membranes are provided with second openings which are situated opposite to the first opening and have diameters smaller than that of the first opening, and that the treatment cylinder is provided with a rigid support element against which the entire sleeve is sealingly pressed with the aid of clamping means. By virtue of their elasticity, these membranes adapt to the form of the extremity so as to function as a membrane sleeve, while between the two rubber membranes an air cushion is created which also serves as a closing means that will not compress. The treatment cylinder is then closed in such a way that the intensity of the pressure variation is attained and kept constant during a specific period of time without a need for inflation of the sleeve, while an obstruction of the venous return to the heart is prevented by this solution for the entire duration of the treatment.

It is particularly advantageous to select a rubber disk, since this can be supported on an annular ridge provided at the entrance of the treatment cylinder and then pressed against this ridge with the aid of a rigid ring and clamps in such a way that the annular ridge penetrates into the rubber and thus seals the treatment cylinder hermetically.

It is advantageous, too, to provide the opening of the treatment is cylinder opposite to the closing device with an identical device which gives access to the interior of the treatment cylinder and can be provided with a heating or cooling device.

The closing device can advantageously be characterised by the fact that the treatment cylinder is axially mobile so as to facilitate introduction of an extremity.

It is particularly advantageous to continuously keep the treatment cylinder in a high position even during a hypobaric phase, while the blocking system of the high position at the same time blocks the treatment cylinder axially.

With this continuous high position of the treatment cylinder, even during the hypobaric phase, on one hand one attains a expanded state of capillaries, venules, and veins by means of the decompression, and an arteriolar dilation and thus a hyperemia by reflex action, on the other hand one attains at the same time an increased venous return to the heart, which in its volume is practically proportional to the arterial capacity of the vessels of the extremity, since the veins of the extremity remain pervious thanks to the closing device of the invention.

It is particularly advantageous that the closing device need not be inflated, which substantially simplifies the electronic controls, since these controls only regulate the hyperbaric and hypobaric phases as well as the periods of time during which they are kept constant, which largely eliminates possible breakdowns or malfunction. These features lead to a device exhibiting a precise and safe functioning.

DESCRIPTION OF THE DRAWINGS

Further details will become evident from the dependent claims and subsequent description of an exemplified embodiment represented in the drawing.

Shown are in FIG. 1 a sectional view of a treatment cylinder with closing device, in FIG. 2 a front view of the treatment cylinder with closing device according to FIG. 1, in FIG. 3 a sectional view of the closing device with an extremity during a hyperbaric phase in the cylinder, in FIG. 4 a sectional view of the closing device with an extremity during a hypobaric phase in the cylinder, in FIG. 5 a partly sectional side elevation of a device with treatment cylinder and closing device, in FIG. 6 a plan view of the device of FIG. 5 with a double treatment cylinder for two extremities, in FIG. 7 a schematic representation of the control elements of the device, in FIG. 8 a sectional view of a control valve for regulation of the intensity of compression and decompression in the closed position, in FIG. 9 a sectional view of the control valve of FIG. 8 in the open position, in FIG. 10 a sectional view of an electric control valve for regulation of the intensity of compression and decompression.

DETAILED DESCRIPTION OF THE INVENTION

Figure 1:
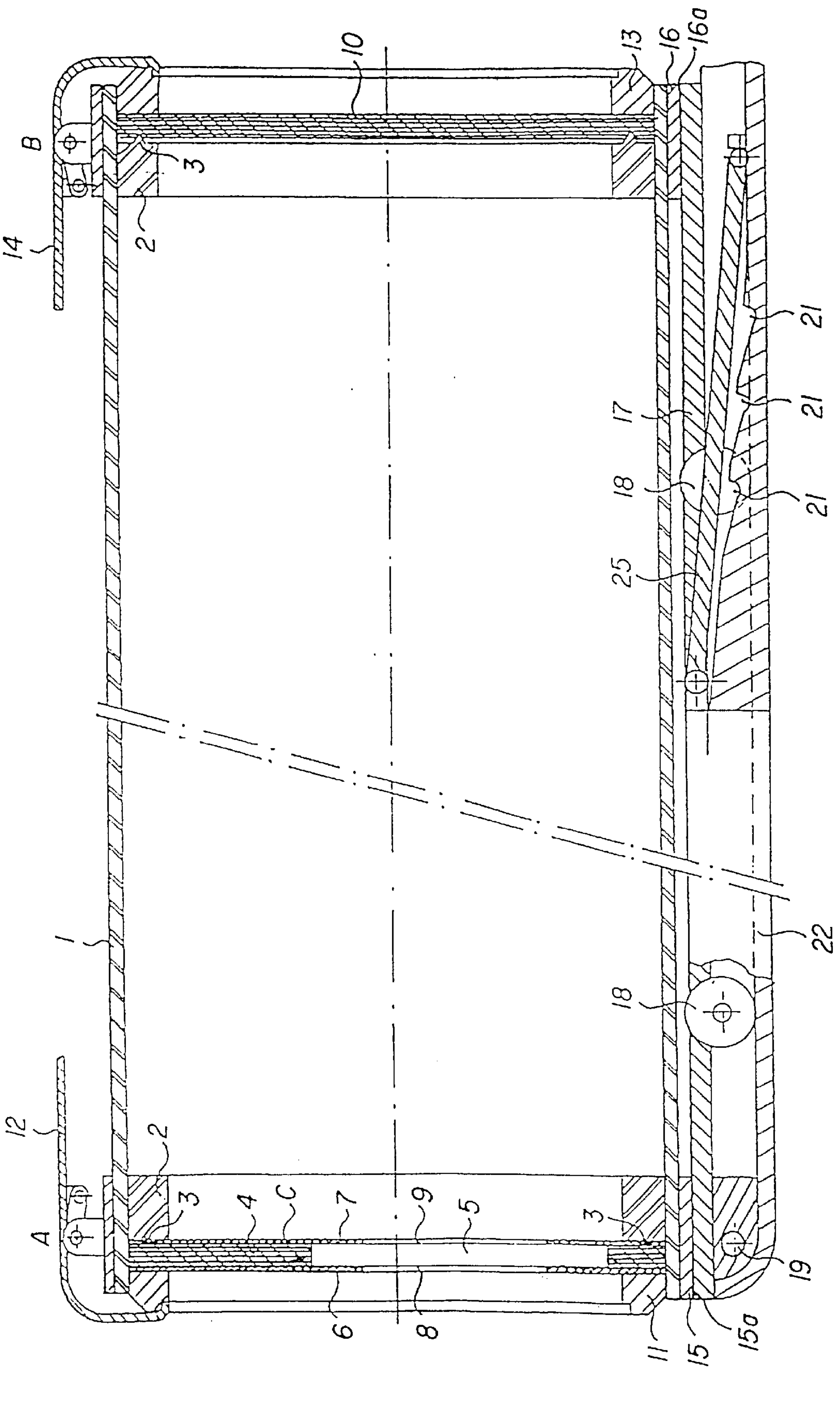
Figure 2:
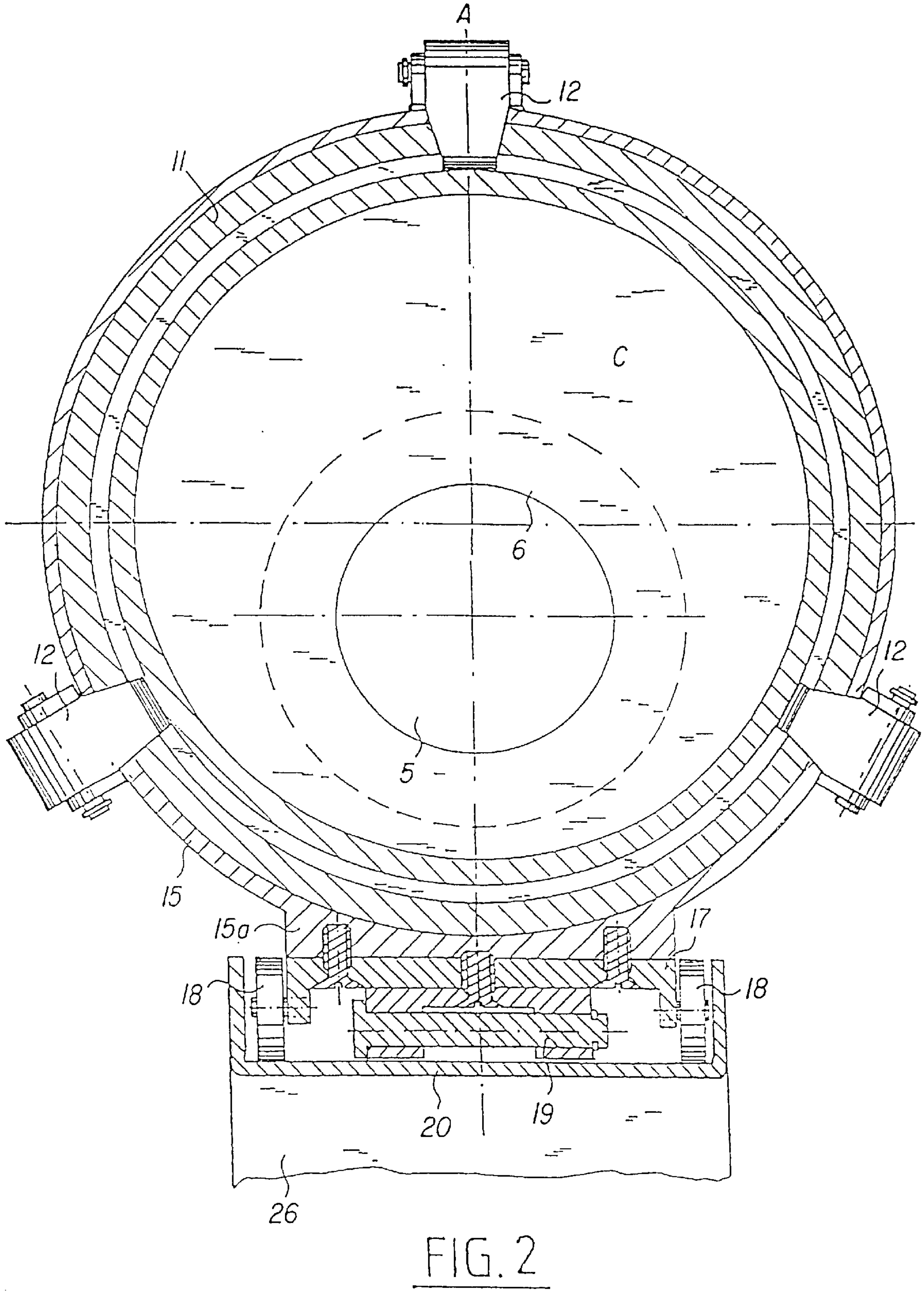
Figure 3:
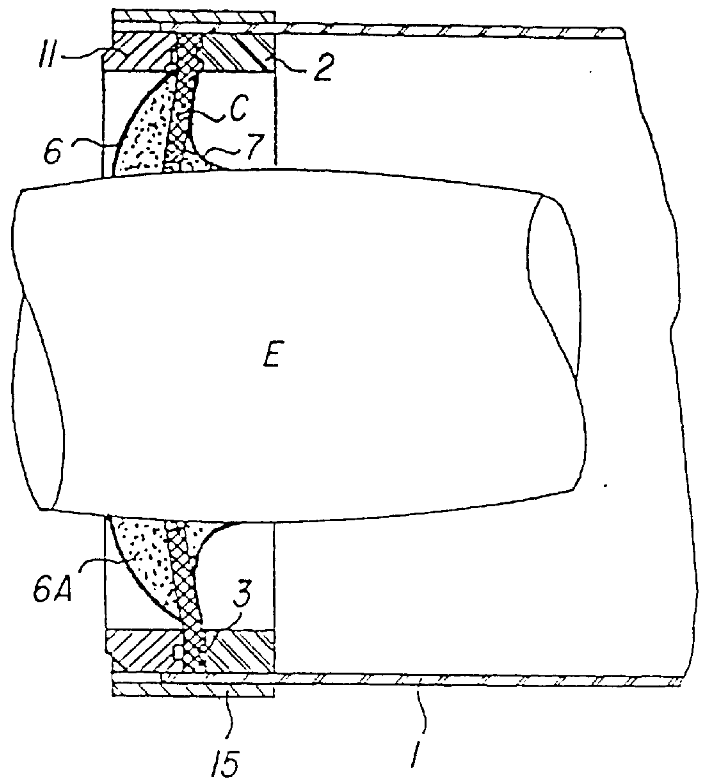
Figure 4:
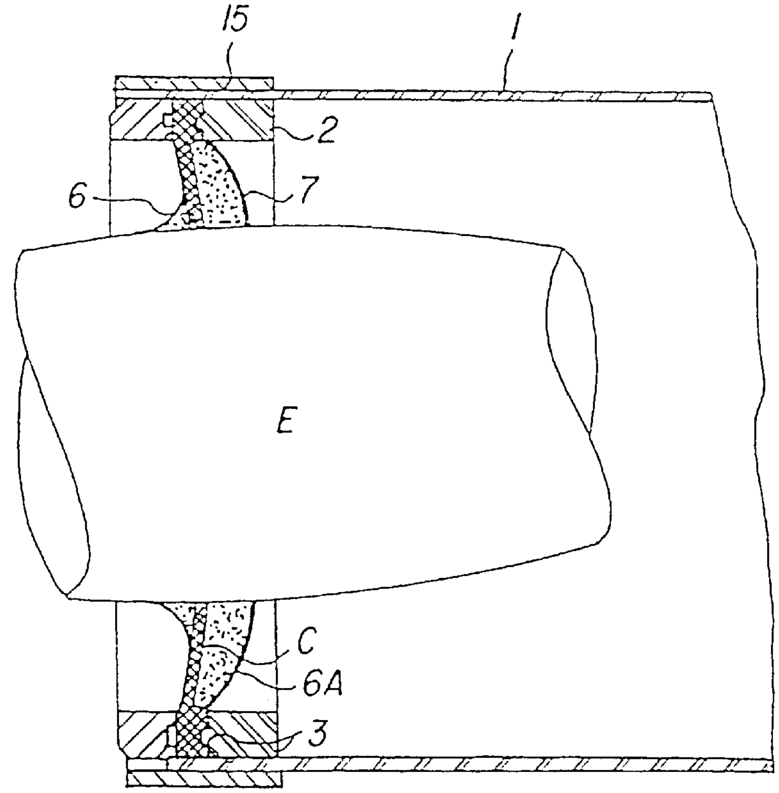

FIG. 1 shows a treatment cylinder 1, preferably made of Plexiglas, which at ends A and B is provided with a ring 2 made of the same material and provided with an annular ridge 3. End A supports a thick-walled rubber disk 4 that has an opening 5. The flat sides of rubber disk 4 are lined with highly elastic, thin-walled rubber membranes 6 and 7, this lining being applied only to an outer ring of the rubber disk 4 as shown in FIGS. 3 and 4. The diameters of openings 8 and 9 of rubber membranes 6 and 7 are smaller than the diameter of opening 5 of the rubber disk 4. This arrangement serves as closing sleeve C enveloping an extremity E to be treated as shown in FIGS. 3 and 4. FIG. 3 shows that the rubber membrane 7 during a hyperbaric phase in cylinder 1 adapts to the form of the extremity E and that the rubber membrane 6 inflates thanks to an intentional leak between the extremity E and the rubber membrane 7 so that an air cushion 6A is created between the two which serves as a noncompressing seal. During a hypobaric phase this process occurs in the opposite direction as illustrated by FIG. 4.

End B of the treatment cylinder 1 also supports a thick-walled rubber disk 10 which, however, has no opening 5 and hence hermetically seals the treatment cylinder 1 at end B.

The sleeve C is pressed against the annular ridge 3 by means of a rigid ring 11 and clamps 12, and the ridge penetrates into the rubber material and hence secures a hermetic seal at this point.

The rubber disk 10 at end B of the cylinder 1 is pressed against an annular ridge 3 by means of a rigid ring 13 and clamps 14, so that end B is hermetically sealed.

It is advantageous that end B can be opened, especially in the case of paralysed patients which cannot move the extremity to be treated, and thus cannot place it correctly into the treatment cylinder 1.

The periphery of the treatment cylinder 1 is provided with a metal ring 15 at end A and with a metal ring 16 at end B, while a flat part 17 is fastened to bulges 15*a* and 16*a* of these rings.

The flat part 17 is provided with rollers 18 which move along a supporting beam 22 and enable the treatment cylinder 1 to be moved axially, thus facilitating the introduction of an extremity.

Figure 5:
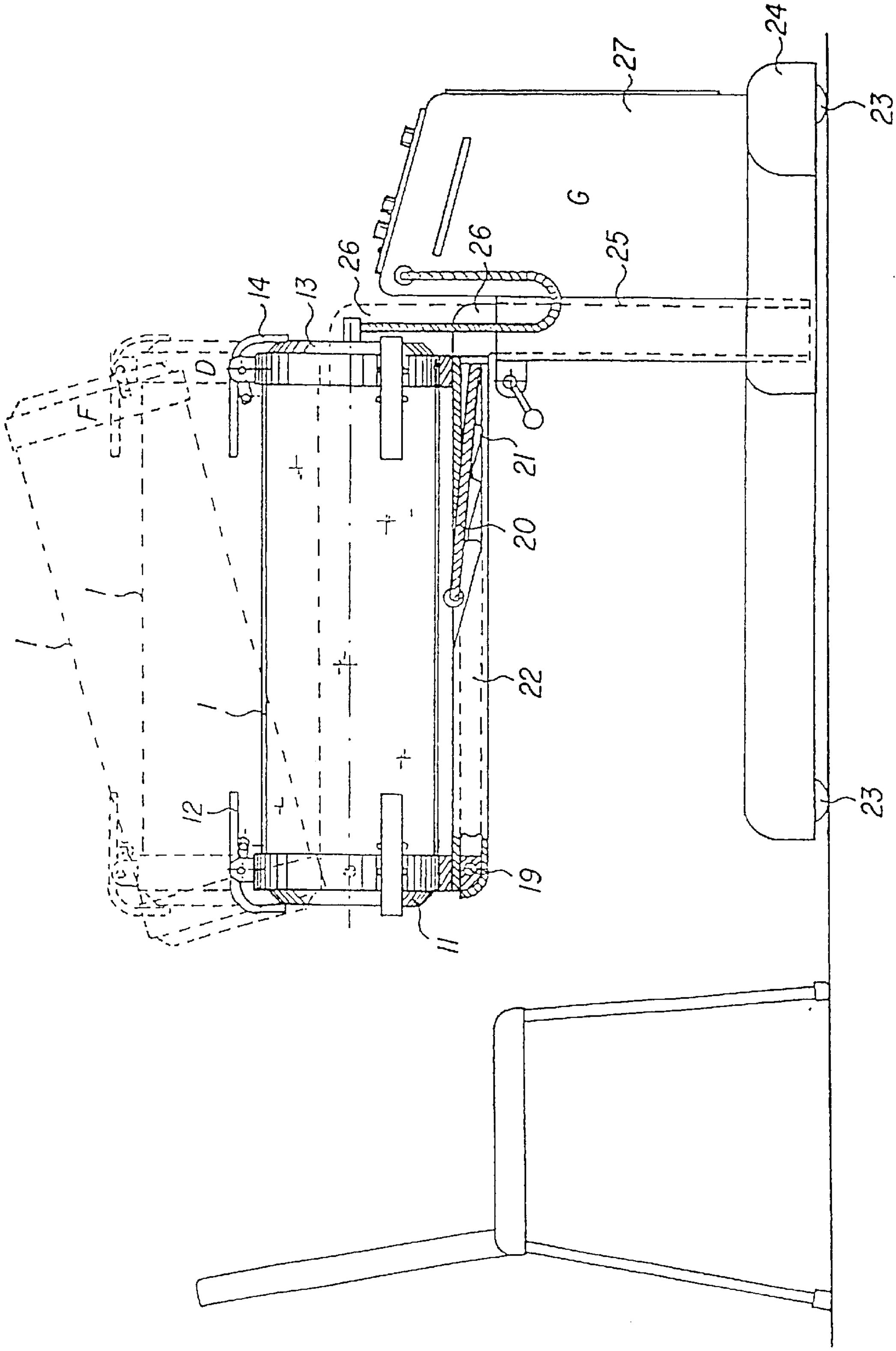

The flat part 17 has an articulation 19 at end A which allows the treatment cylinder 1 to be moved to a high position as shown in dashed lines in FIG. 5, in which case a strut 20 engages into grooves 21 of the supporting beam 22 and hence will also prevent an axial motion of the treatment cylinder.

The use of rollers 18 enabling an axial displacement of the treatment cylinder 1 is intended in particular for portable treatment cylinders 1, in which case the control means and the vacuum pump and pressure pump are to be found in a housing which also is portable, but not shown. Such an embodiment may have utility when a patient unable to walk must be treated in his home, or during sports events when a hyperbaric and hypobaric treatment is highly effective in the case of sprains, cramps or contusions with hematomas.

If, on the other hand, the treatment cylinder as shown in FIG. 5 is supported by a device G in which the supporting beam 22 is movably connected with the device G, the rollers 18 can be omitted inasmuch as the entire device G provided with rollers 23 is mobile, so that for easier introduction of an extremity into the treatment cylinder 1 the entire device G can be displaced. A blocking device (not shown) prevents a shifting of the device G.

The embodiment according to FIG. 5 is advantageous, since the treatment cylinder 1 can be vertically displaced, which as shown allows a patient to be treated who is seated on a chair, or the treatment cylinder 1 to be arranged so high up that the patient can be stretched out on a massage table or bed, as illustrated with the height D. Lastly, position F of the treatment cylinder 1 shows the high position into which it can be brought for the entire duration of the treatment session.

Figure 7:
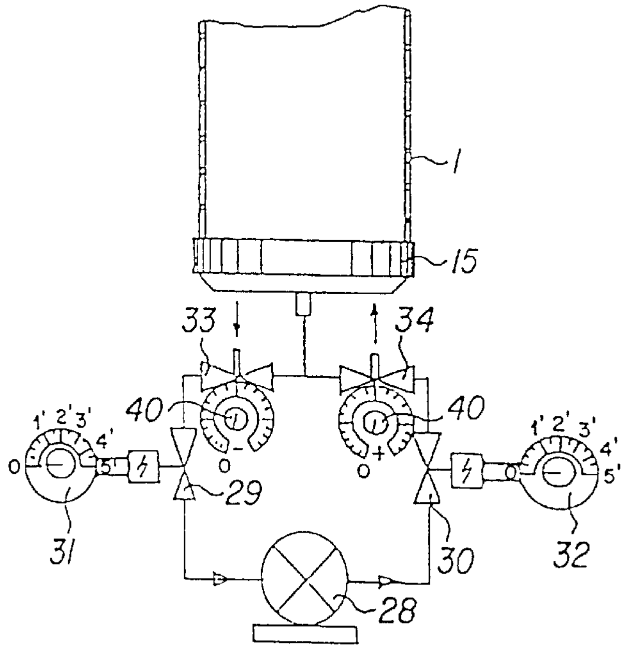

Device G has a base 24 provided with the rollers 23 and with a seat in which a support 26 is movably retained. A housing 27 in which as shown in FIG. 7 a vacuum and pressure pump 28, a magnetic valve 29 for decompression and a magnetic valve 30 for compression are to be found is mounted onto the base. The magnetic valve 29 is connected with a timing relay 31, the magnetic valve 30 is connected with a timing relay 32. The timing relais 31, 32 allow the decompression compression to be kept constant for a predetermined period of time, for instance in a stage II obliterative arteriopathy with walking distance 200 m one maintains constancy of the hypobaric phase for 45 s and of the hyperbaric phase for 30 s, in which case the timing relay 31 will close the magnetic valve 29 and open the magnetic valve 30, or timing relay 32 will close the magnetic valve 30 and open the magnetic valve 29 when the set times have elapsed.

Figure 8:
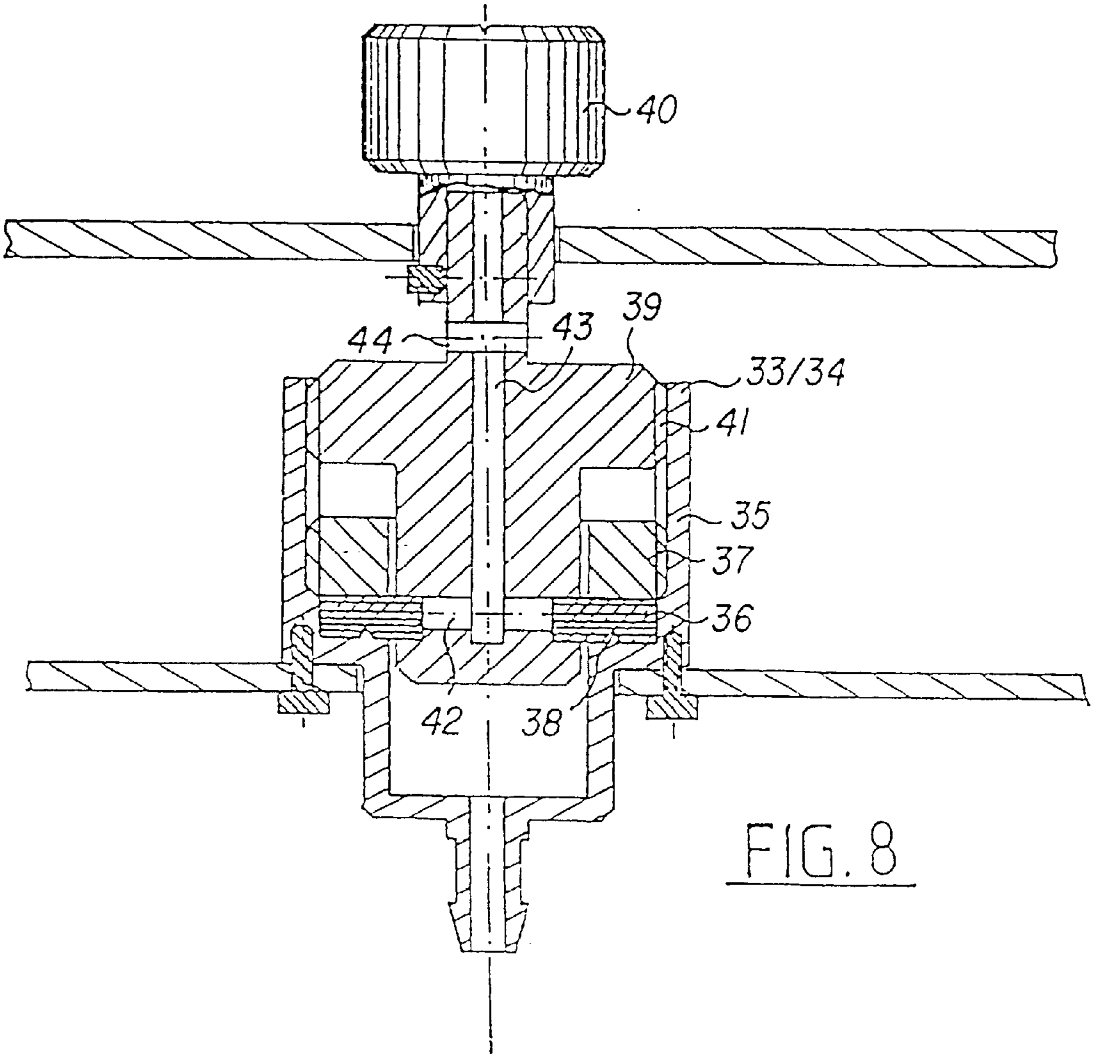
Figure 9:
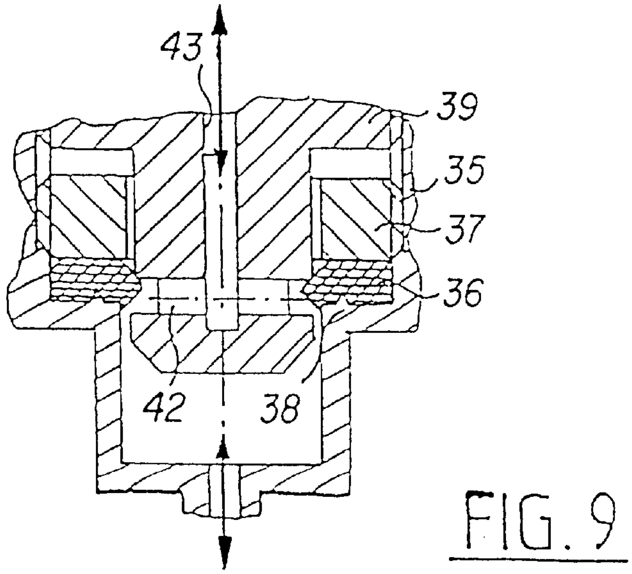

The intensities of the compression and decompression are regulated via control valves 33 and 34 as illustrated in FIGS. 8 and 9. Valves 33 and 34 consist of a valve body 35, an elastomer seal 36 which is pressed into its seat 38 by a screw member 37, a piston 39 and a rotary head 40.

The control valves 33 and 34 are in the open position as shown in FIG. 9 before the pressure values are set. This position is set by means of the piston 39 which has a thread 41 and is moved by the turning head 40. To this effect the piston 39 deforms the elastomer seal 36 in such a way that a lower transverse bore 42 of the piston 39 which opens into an axial channel 43 and hence into an upper transverse 44 is opened. When turning the rotary head clockwise, for instance, the seal 36 gradually returns to its initial position and thus progressively closes off the lower transverse bore 42. The flow cross section of this bore is varied in such a way that a degree of throttling is achieved which corresponds to the compression or decompression that ought to be attained. In the instance of control valve 33, pump 28 draws air from the outside via the upper transverse bore 44, the axial channel 43 and the lower transverse bore 42 when the magnetic valve 29 is open, while in the instance of control valve 34, pump 28 rejects air to the outside via the lower transverse bore 42, the axial channel 43 and the upper transverse bore. Via these intended leaks one can set the desired pressure values, in which case compressor 28 will maintain the set pressure values constant despite the leaks.

It goes without saying that the pitch of thread 41 is selected so that a rotation through 300° will allow a maximum excess pressure of 152 mmHg. Higher pressure values are prevented by safety valves (not shown).

Figure 10:
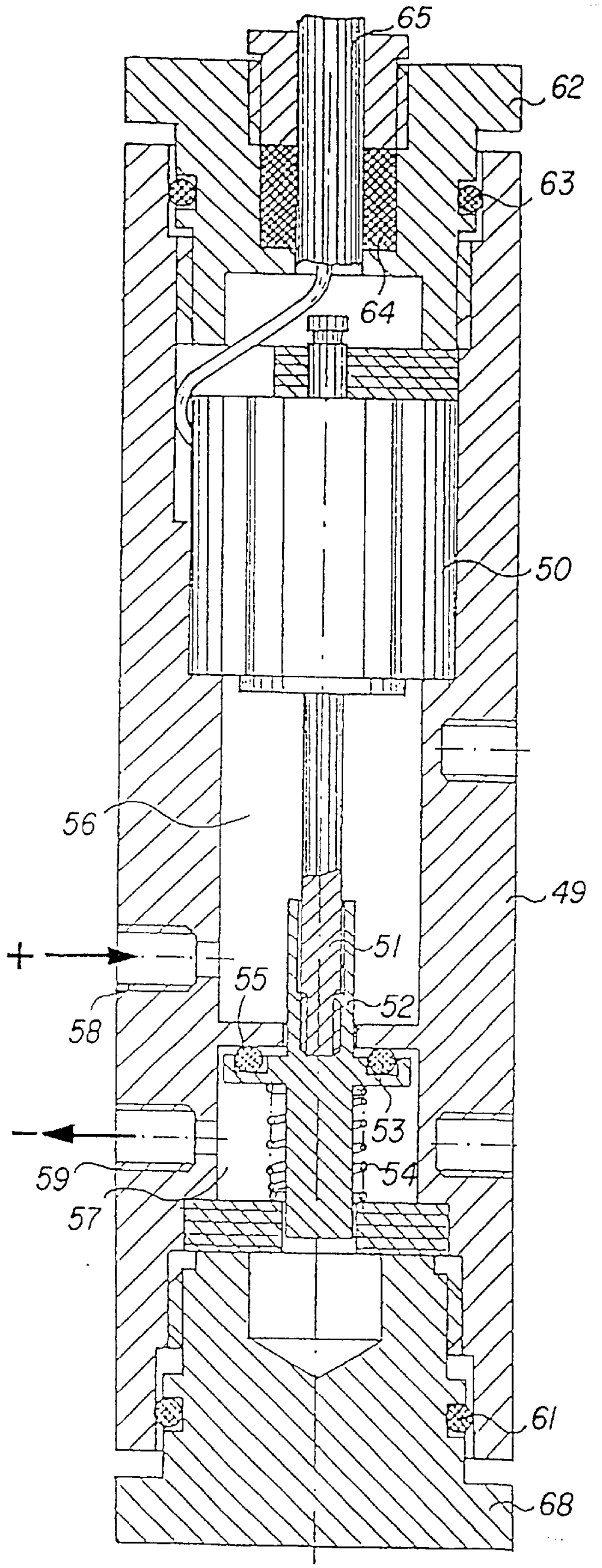

FIG. 10 shows an entirely novel, electronically regulated control valve for setting the compression and decompression values. It consists of a valve body 49 holding an electric traction magnet 50 on the armature axis 51 of which there is a piston 52 provided with an O-ring 53 and pressed into its seat 55 by means of a spring 54, the force of the spring being selected so that on one hand it counterbalances the weight of the piston 52 and on the other hand it presses O-ring 53 to the seat 55 in such a way that compression must prevail in chamber 56, and decompression in chamber 57, before O-ring 53 will be pushed from its seat 55. To this effect chamber 56 has a tapped hole 58 through which an excess pressure coming from the treatment cylinder will enter, and chamber 57 has a tapped hole 59 through which the treatment cylinder 1 draws air. The regulation of the pressure values is accomplished via a variable supply voltage to traction magnet 50, for instance 24 V for a pressure or suction of 152 mmHg and 9 V for a pressure or suction of 0.38 mmHg (0.05 atmospheres excess pressure). As soon as the set pressure values are attained in chambers 56 and 57 they will push or pull piston 52, and thus O-ring 53, from its seat 55, so that excessive compression or decompression can be relieved via magnetic valves and 34, and the set pressure values can be kept constant. Valve body 49 is sealingly closed off on the side of chamber 57 with a screw lid 88 and an O-ring 61. The opposite side of valve body 49 is sealingly closed off with a screw lid 62 and an O-ring 63, and screw lid 62 is provided with a gland 64 which serves to seal the valve body along a cable lead 65 of the traction magnet 50.

Figure 6:
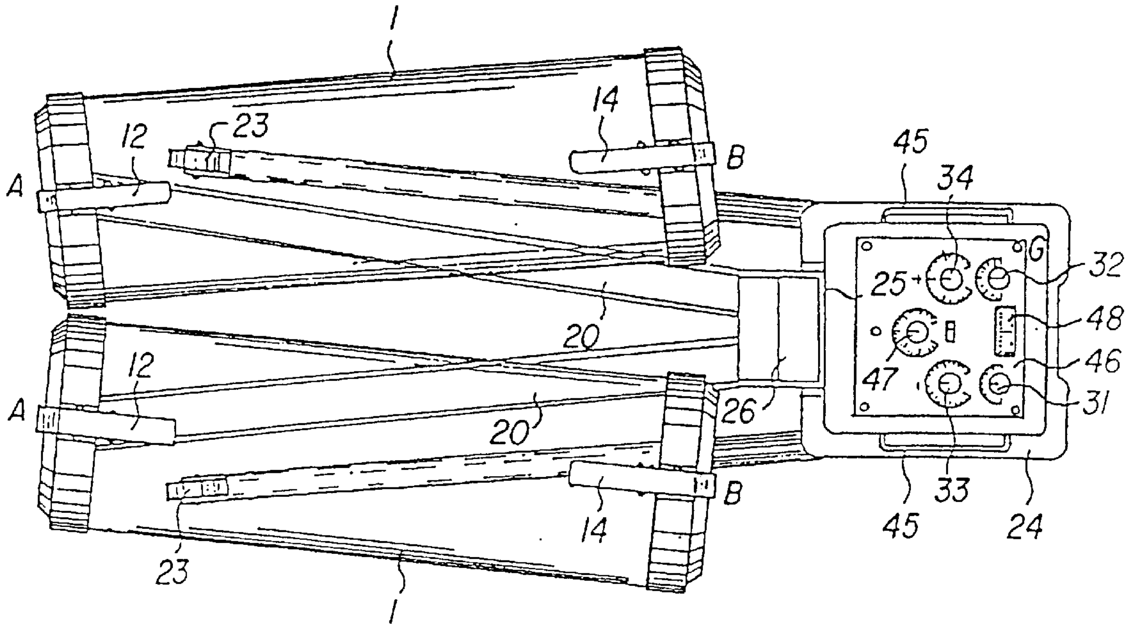

FIG. 6 shows the device G provided with two treatment cylinders 1 in order to treat two extremities simultaneously, which via a reflex action of the more healthy extremity may lead to a favorable effect on the more strongly affected extremity. A panel 46 reveals a time switch 47 with which the duration of a session is set, a pressure indicator 48 as well as the scales 33 and 34 of the control valves and their timing relays 31 and 32.

Device G is delivered with a treatment table which enables the device G to be used at once for the treatment of peripheral circulatory disorders, as this table takes into account the pathology and its severity. It is left to the physician to adapt the compression and decompression values and the periods of time during which they are to be kept constant, individually to each case.

A treatment session always starts with a compression phase which is followed by a decompression phase, while the period of time during which the compression and decompression are kept constant depends on the pathology and its severity, so that on one hand the rubber membranes 6 and 7 will optimally adapt to the shape of the extremity to be treated, and on the other hand the metabolites which are produced in excessive amounts on account of circulatory disorders will be eliminated.

The embodiment examples described above should of course not have any limiting character but may be subject to any desirable modification within the scope defined by the independent claim. Thus, the disk 4 and the membranes 6, 7 may consist of any appropriate material, for instance a synthetic or natural elastomer. It has also been found to be advantageous to make disk 4 and membranes 6, 7 of the same rubber, with a Shore hardness of less than 50°. Advantageously the diameter of the opening 5 of disk 4 is at least 4 cm larger than that of openings 8, 9 of the membranes 6, 7. The devices for air admission and evacuation as well as the control and regulation means can be realised in a different way, for instance with pulsed electric valves of adjustable frequency that are controlled by computer. The treatment cylinders could also have a cross section that is not round but, for instance, polygonal or rectangular. The openings of the disk and membranes can be centered or eccentric, where a centered arrangement may improve the venous return, depending on the outfitting of the treatment cylinders, and in these cylinders padded support means can also be provided for the body limb to be treated.

What is claimed is:

1. Device for treating peripheral circulatory disorders, consisting of at least one treatment cylinder (1) into which a body limb (E) to be treated can be introduced at least in part via a closing device and in which a compression and/or decompression can be brought about by means of control elements (28–34) via a device for the admission and evacuation of air, characterised by the fact that the closing device presents a sleeve (C) that has a thick-walled disk (4) covered on the two flat sides with thin-walled, highly elastic membranes (6, 7), that the disk (4) is provided with a first opening (5) and the membranes (6, 7) are provided with second openings (8, 9) situated opposite to the first opening (5) and having diameters that are smaller than that of the first opening (5), while the closing device presents a rigid support element (2) fixed at the treatment cylinder (1) against which the entire sleeve (C) is sealingly pressed by clamping means (11, 12), and characterised by the fact that the membranes (6, 7) are fixed on disk (4) only along an outer ring of this disk while the remainder of the membranes (6, 7) is freely floating relative to disk (4) so that the second openings (7, 8) of the membranes (6, 7) adapt to the form of the body limb and between the membranes an air cushion (6A) is formed.

2. Device according to claim 1, characterised in that the support element is formed by a rigid ring (2) with at least one annular ridge (3) against which the sleeve (C) is sealingly pressed by the clamping means.

3. Device according to claim 2, characterised in that the membranes (6, 7) are fixed on disk (4) only over the width that is pressed against the rigid support element (2).

4. Device according to claim 1, characterised in that the membranes (6, 7) are fixed on disk (4) only over the width that is pressed against the rigid support element (2).

5. Device according to claim 1, characterised in that the disk (4) and the membranes (6, 7) are made of elastomer, preferably of rubber.

6. Device according to claim 1, characterised in that the treatment cylinder (1) is provided with a ring (2) at a first end (A) and at a second end (B), that the rings (2) present annular ridges (3) against which at the first end (A) the sleeve (C) and at the second end (B) a disk (10) without opening are pressed by means of rigid rings (11, 13) and clamps (12, 13) as the clamping means in such a way that the annular ridges (3) penetrate into the sleeve (C) and into the disk (10).

7. Device according to claim 1, characterised in that both ends (A, B) of the treatment cylinder (1) are provided with metal rings (15, 16) which present bulges (15*a,* 16*a*), that the bulges (15*a,* 16*a*) are connected with a flat part (17), that the flat part (17) is provided with rollers (18) which move along a support beam (22), and that the flat part (17) presents an articulation (19) and a strut (20) which engages into grooves (21) of the support beam (22).

8. Device according to claim 1, characterised in that the treatment cylinder (1) is movably retained in a seat (25) of the device (G) by means of a support beam (22) and a support (26), that the device (G) is fitted with blockable rollers (23), that a housing (27) fastened to a base (24) of the device (G) contains control elements (28, 29, 30, 31, 32, 33, 34) which are in connection with a control panel (46) and can be controlled by operating elements (40), while the control elements are equipped in such a way that a vacuum and pressure pump (28) is started up when a time switch (47) is operated, that depending on the setting of the operating elements (40) a hyperbaric and a hypobaric phase of varying intensity are created in alternation in the treatment cylinder (1), while timing relays (31, 32) enable these phases to be kept constant during a predetermined period of time, while a first timing relay (31) closes a first magnetic valve (29), opens a second magnetic valve (30), and starts a second timing relay (32) which, at the end of a predetermined time of constancy, closes the second magnetic valve (30), opens the first magnetic valve (29) and starts the first timing relay (31), and the alternating hyperbaric and hypobaric phases are discontinued at the end of a treatment duration set on a time switch (47).

9. Device according to claim 8, characterised in that the device for air admission and evacuation presents valves (33, 34) with a valve body (35) in which a seal (36) is placed in a seat (38) and pressed into this seat by a screw member (37), that the seal (36) engages into a piston (39) and in this way closes off a lower transverse bore (42) which is in connection with an axial channel (43) opening into an upper transverse bore (44), that the piston (39) has a thread (41) by which it can be screwed into the valve body (35) via a rotary head (40) in such a way that the piston (39) deforms the seal (36) so that at least a part of the lower transverse bore (42) is opened and that this seal when unscrewing the piston (39) from the valve body (35) will once more close off the lower transverse bore (42).

10. Device according to claim 1, characterised in that the device for air admission and evacuation presents valves (33, 34) with a valve body (35) in which a seal (36) is placed in a seat (38) and pressed into this seat by a screw member (37), that the seal (36) engages into a piston (39) and in this way closes off a lower transverse bore (42) which is in connection with an axial channel (43) opening into an upper transverse bore (44), that the piston (39) has a thread (41) by which it can be screwed into the valve body (35) via a rotary head (40) in such a way that the piston (39) deforms the seal (36) so that at least a part of the lower transverse bore (42) is opened and that this seal when unscrewing the piston (39) from the valve body (35) will once more close off the lower transverse bore (42).

11. Closing device for a treatment cylinder (1) of a device for treating peripheral circulatory disorders according to claim 1 with at least one treatment cylinder (1) into which a body limb (E) to be treated can be introduced at least in part via the closing device and in which a compression or/and decompression can be brought about by means of control elements (28–34) via a device for the admission and evacuation of air, characterised in that the closing device presents a sleeve (C) having a thick-walled disk (4) which is covered on the two flat sides with thin-walled, highly elastic membranes (6, 7), that the disk (4) is provided with a first opening (5) and the membranes (6, 7) are provided with second openings (8, 9) that are located opposite to the first opening (5) and have diameters smaller than the diameter of the first opening (5), while the closing device presents a rigid support element (2) fixed at the treatment cylinder (1) against which the entire sleeve (C) is sealingly pressed by clamping means (11, 12), and characterised by the fact that the membranes (6, 7) are fixed on disk (4) only along an outer ring of this disk while the remainder of the membranes (6, 7) is freely floating relative to disk (4) so that the second openings (7, 8) of the membranes (6, 7) adapt to the form of the body limb and between the membranes an air cushion (6A) is formed.

12. Closing device according to claim 11, characterised in that the disk (4) and the membranes (6, 7) are made of the same rubber having a Shore hardness of less than 50°.

13. Closing device according to claim 11, characterised in that the diameter of the first opening (5) of the disk (4) is at least 4 cm larger than the second openings (8, 9) of the membranes (6, 7).

* * * * *